U S009974649B2

United States Patent
Racchini et al.

(10) Patent No.: US 9,974,649 B2
(45) Date of Patent: May 22, 2018

(54) STENTED PROSTHETIC HEART VALVE HAVING WRAP AND METHODS OF DELIVERY AND DEPLOYMENT

(71) Applicant: Medtronic Vascular, Inc., Santa Rosa, CA (US)

(72) Inventors: Joel Racchini, Edina, MN (US); Kshitija Garde, Fullerton, CA (US); Paul Rothstein, Elk River, MN (US); Jeffrey Sandstrom, Scandia, MN (US); Cynthia Clague, Minnetonka, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 35 days.

(21) Appl. No.: 15/079,090

(22) Filed: Mar. 24, 2016

(65) Prior Publication Data
US 2017/0273784 A1 Sep. 28, 2017

(51) Int. Cl.
*A61F 2/24* (2006.01)
(52) U.S. Cl.
CPC .......... *A61F 2/2418* (2013.01); *A61F 2/2427* (2013.01); *A61F 2220/0075* (2013.01)
(58) Field of Classification Search
CPC .......... A61F 2/24; A61F 2/243; A61F 2/2436; A61F 2/2439; A61F 2/2412; A61F 2/2418; A61F 2/2427
See application file for complete search history.

(56) References Cited

U.S. PATENT DOCUMENTS

| 7,276,078 | B2 | 10/2007 | Spenser et al. |
| 7,780,725 | B2 | 8/2010 | Haug et al. |
| 8,449,599 | B2 | 5/2013 | Chau et al. |
| 8,603,160 | B2 | 12/2013 | Salahieh et al. |
| 8,795,357 | B2 | 8/2014 | Yohanan et al. |
| 8,808,356 | B2 | 8/2014 | Braido et al. |
| 8,992,608 | B2 | 3/2015 | Haug et al. |
| 2005/0137688 | A1 | 6/2005 | Salahieh et al. |
| 2009/0192591 | A1 | 7/2009 | Ryan et al. |
| 2009/0264997 | A1 | 10/2009 | Salahieh et al. |
| 2012/0123529 | A1 | 5/2012 | Levi et al. |
| 2013/0030519 | A1 | 1/2013 | Tran et al. |
| 2013/0190857 | A1 | 7/2013 | Mitra et al. |
| 2013/0245753 | A1 | 9/2013 | Alkhatib |

(Continued)

FOREIGN PATENT DOCUMENTS

| WO | 2009044082 | 4/2009 |
| WO | 2015152980 | 10/2015 |

OTHER PUBLICATIONS

International Search Report and Written Opinion for PCT/US20171022784 dated Jul. 6, 2017 (14 pgs).

*Primary Examiner* — Jason-Dennis Stewart
(74) *Attorney, Agent, or Firm* — Dicke, Billig & Czaja, PLLC

(57) ABSTRACT

Systems and methods of delivering and deploying a stented prosthetic heart valve having a wrap that is automatically deployed to prevent or mitigate paravalvular leakage. In various embodiments, during transcatheter delivery of the stented prosthetic heart valve, the wrap is extends beyond a stent frame of the stented prosthetic heart valve so that the profile of the stented prosthetic heart valve is not increased during delivery. The disclosed embodiments are arranged and configured so that upon expansion of a stent frame of the stented prosthetic heart valve, a plurality of elongated members automatically pull the wrap distally into a deployed arrangement.

22 Claims, 14 Drawing Sheets

(56) References Cited

U.S. PATENT DOCUMENTS

| | | |
|---|---|---|
| 2013/0274873 A1 | 10/2013 | Delaloye et al. |
| 2013/0331929 A1 | 12/2013 | Mitra et al. |
| 2014/0114402 A1 | 4/2014 | Ahlberg et al. |
| 2014/0277419 A1 | 9/2014 | Garde et al. |
| 2014/0277422 A1 | 9/2014 | Ratz et al. |
| 2014/0277423 A1 | 9/2014 | Alkhatib et al. |
| 2015/0005863 A1 | 1/2015 | Para |
| 2015/0073540 A1 | 3/2015 | Salahieh et al. |
| 2015/0122687 A1 | 5/2015 | Zeng et al. |
| 2015/0142104 A1 | 5/2015 | Braido |
| 2015/0282932 A1 | 10/2015 | Neuman et al. |

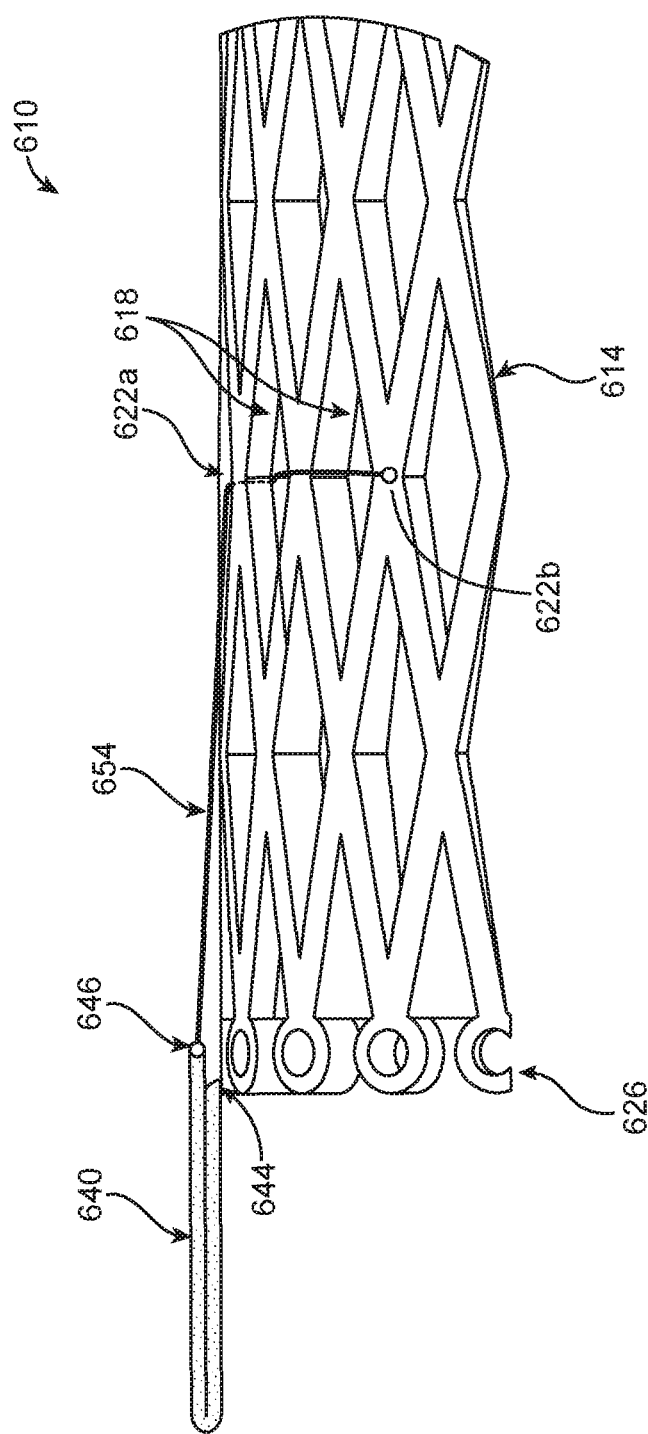

STENTED PROSTHETIC HEART VALVE HAVING WRAP AND METHODS OF DELIVERY AND DEPLOYMENT

BACKGROUND

The present disclosure generally relates to systems and methods for transcatheter delivery and deployment of a stented prosthetic heart valve having a wrap for preventing and/or mitigating paravalvular leakage.

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent." Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al.

Although transcatheter delivery methods have provided safer and less invasive methods for replacing a defective native heart valve, leakage between the implanted prosthetic valve and the surrounding native tissue is a recurring problem. Leakage sometimes occurs due to the fact that minimally invasive and percutaneous replacement of cardiac valves typically does not involve actual physical removal of the diseased or injured heart valve. Rather, the replacement stented prosthetic valve is delivered in a compressed condition to the valve site, where it is expanded to its operational state within the valve. Calcified or diseased native leaflets are pressed to the side walls of the native valve by the radial force of the stent frame of the prosthetic valve. These calcified leaflets do not allow complete conformance of the stent frame with the native valve and can be a source of paravalvular leakage (PVL). Significant pressure gradients across the valve cause blood to leak through the gaps between the implanted prosthetic valve and the calcified anatomy.

Embodiments hereof are related to systems and methods for transcatheter delivery and deployment of a stented prosthetic heart valve having a wrap for preventing and/or mitigating paravalvular leakage.

SUMMARY

The disclosure relates to systems and methods of delivering and deploying a stented prosthetic heart valve having a wrap that is automatically deployed to mitigate or assist in the prevention of paravalvular leakage. In various embodiments, during transcatheter delivery of the stented prosthetic heart valve, the wrap is secured either in front of or behind (i.e. distal to or proximal to) a stent frame of the stented prosthetic heart valve. The disclosed embodiments are arranged and configured so that upon expansion of the stent frame from a compressed, delivery arrangement, a plurality of elongated members spaced around the stent frame automatically pull the wrap proximally over and around the stent frame. In other embodiments, the wrap is pulled upwardly, inverting itself in the process.

Embodiments disclosed herein can reliably deploy the wrap and effectively reduce stasis without adding an additional step to the delivery process that needs to be performed by a clinician. Further embodiments are also beneficial since they do not increase the profile of the stented prosthetic heart valve during delivery as compared to a similar stented prosthetic heart valve having a fixed wrap, which is particularly important for transcatheter delivery procedures.

BRIEF DESCRIPTION OF THE DRAWINGS

FIG. 8A is a partial, schematic illustration of another embodiment of a stented prosthetic heart valve having a wrap secured to a stent frame with a plurality of elongated members, the stented prosthetic heart valve in a compressed, delivery arrangement and the wrap extending beyond the stent frame (valve leaflets of the stented prosthetic heart valve are not shown for clarity).

DETAILED DESCRIPTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from, or in a direction away from the clinician. "Proximal" and "proximally" are a position near or in a direction toward the clinician. Although the present disclosure has been described with reference to preferred embodiments, workers skilled in the art will recognize that changes can be made in form and detail without departing from the spirit and scope of the present disclosure.

Figure 1A:
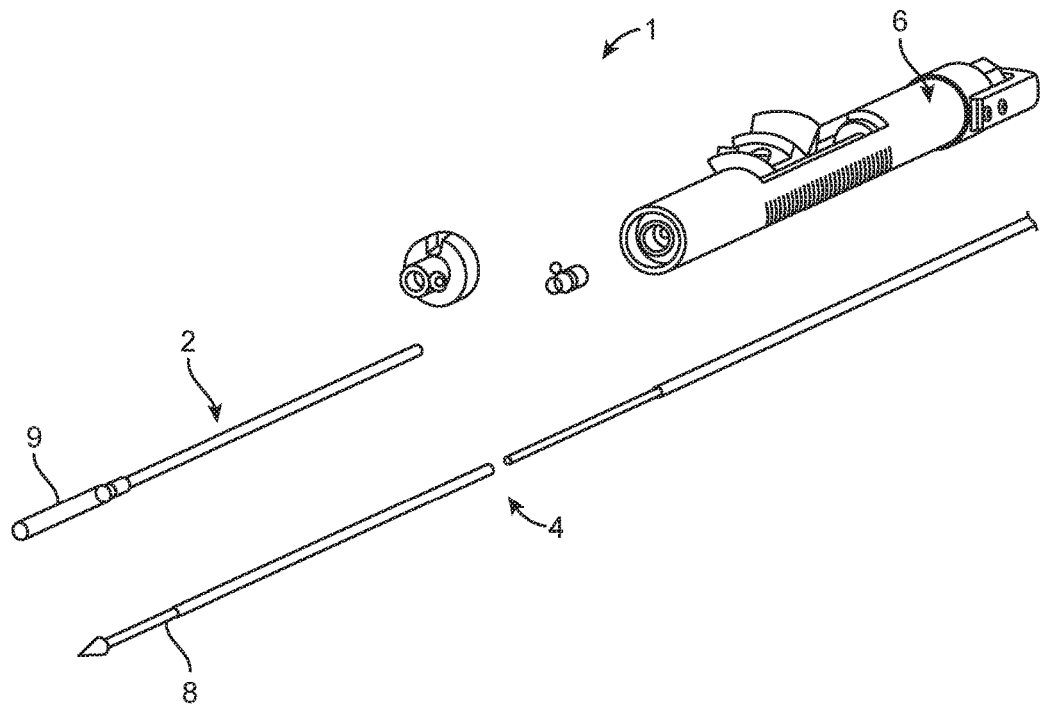
FIG. 1A is an exemplary delivery device for delivering and deploying a stented prosthetic heart valve (not shown), the delivery device having an inner shaft assembly and an optional outer sheath assembly.
Figure 1B:
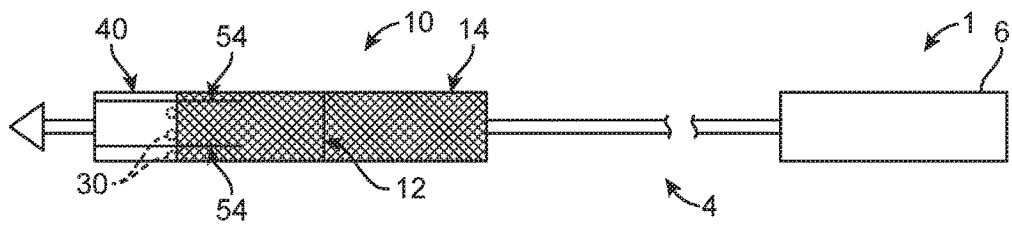
FIG. 1B is a schematic illustration of the delivery device of FIG. 1A with the stented prosthetic heart valve having a paravalvular leak preventing wrap loaded thereto, the stented prosthetic heart valve and the wrap secured to an inner shaft assembly in a delivery arrangement (the outer sheath assembly not shown).
Figure 1C:
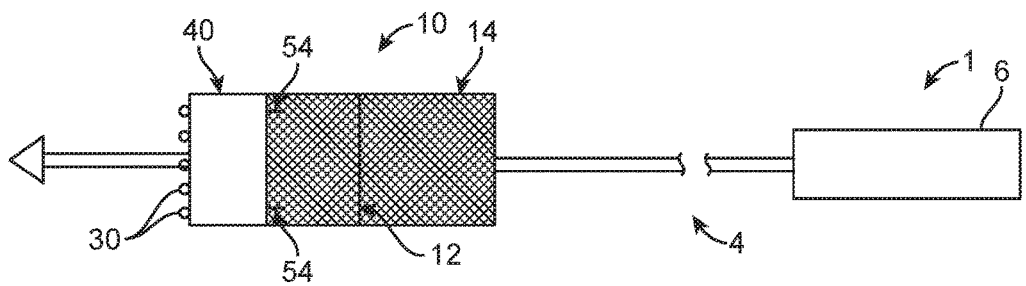
FIG. 1C is a schematic illustration of the delivery device of FIGS. 1A-1B with the stented prosthetic heart valve and the wrap in a deployed arrangement, prior to release from the delivery device.

By way of background, general components of one non-limiting example of a delivery device 1 with which the present disclosures are useful are illustrated in FIGS. 1A-1E. The delivery device 1 is arranged and configured for percutaneously delivering a stented prosthetic heart valve 10 (hereinafter "prosthetic valve") to a patient's native defective heart valve. The delivery device 1 includes an optional outer sheath assembly 2, an inner shaft assembly 4, and a handle assembly 6. One or more sutures 12 are provided, and can be considered part of the delivery device 1 in some embodiments or as part of the prosthetic valve 10 in other embodiments. The delivery device 1 provides a loaded delivery arrangement (FIG. 1B) in which the prosthetic heart valve 10 is loaded over the inner shaft assembly 4 and is compressively retained on a spindle 8 or the like by the sutures 12. As is schematically illustrated in FIGS. 1B-1C the compression on the prosthetic valve 10 can be adjusted with one or more sutures 12. Once loaded and compressed, the prosthetic valve 10 is located at the target site, tension in the sutures 12 is lessened to permit the prosthetic valve 10 to self-expand, partially releasing and ultimately fully deploying the prosthetic valve 10 from the inner shaft assembly 4 (see FIG. 1B). In the illustrated embodiment, the outer sheath assembly 2, where provided, includes a capsule 9 that is selectively disposed over the prosthetic valve 10 that assists in constraining the prosthetic valve 10 in the loaded or compressed arrangement and can be retracted by the handle assembly 6 to expose the prosthetic heart valve 10.

As referred to herein, stented prosthetic heart valves or "prosthetic valves" useful with and/or as part of the various systems and methods of the present disclosure may assume a wide variety of different configurations, such as a biostented prosthetic heart valve having tissue leaflets or a synthetic heart valve having polymeric, metallic, or tissue-engineered leaflets, and can be specifically configured for replacing any heart valve. Thus, the prosthetic valves useful with the systems and methods of the present disclosure can be generally used for replacement of a native aortic, mitral, pulmonic, or tricuspid valve, for use as a venous valve, or to replace a failed bioprosthesis, such as in the area of an aortic valve or mitral valve, for example.

In general terms, the prosthetic valves of the present disclosure include a stent or stent frame maintaining a valve structure (tissue or synthetic), with the stent frame having a normal, expanded arrangement and collapsible to a compressed arrangement for loading within the delivery device. The stent frame is normally constructed to self-deploy or self-expand when released from the delivery device. For example, the prosthetic valve useful with the present disclosure can be a prosthetic valve sold under the trade name CoreValve® available from Medtronic CoreValve, LLC. Other non-limiting examples of transcatheter heart valve prostheses useful with systems and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic valve. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine pericardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, replacement prosthetic valves of the types described herein can incorporate more or less than three leaflets.

Some embodiments of the stent frames can be a series of wires or wire segments arranged such that they are capable of self-transitioning from a compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached leaflets can be mounted onto a delivery device. The stent frame support structures are configured so that they can be changed to their normal, expanded arrangement when desired, such as by the relative movement of one or more sheaths relative to a length of the stent frame.

The stent frame support structures in embodiments of the present disclosure can be formed from a shape memory material such as a nickel titanium alloy (e.g., Nitinol™). With this material, the support structure is self-expandable from the compressed arrangement to the normal, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of some embodiments may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be retracted to allow the stent frame to self-expand. Further details of such embodiments are discussed below.

Figure 1D:
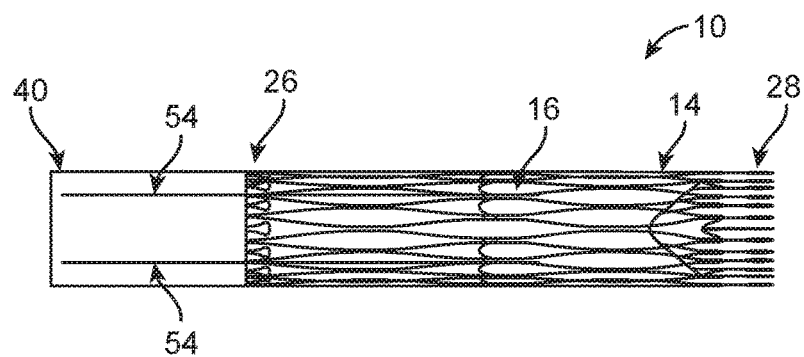
FIG. 1D is a side view of the delivery arrangement of the stented prosthetic heart valve and the wrap of FIG. 1B (a plurality of elongated members interconnecting the wrap to a stent frame of the stented prosthetic heart valve are not shown for clarity).
Figure 1E:
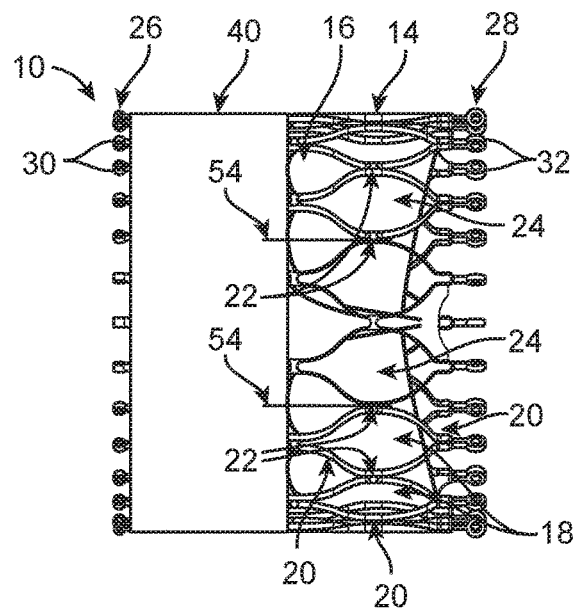
FIG. 1E is a side view of the deployment arrangement of the wrap the stented prosthetic heart valve of FIG. 1C.

The non-limiting prosthetic valve 10 useful with systems and methods of the present disclosure is illustrated in FIGS. 1D-1E. As a point of reference, the prosthetic valve 10 has a compressed, delivery configuration as is shown in FIG. 1D (e.g., when compressively retained on the inner shaft assembly 4, and, perhaps, within a capsule 9). The prosthetic valve 10 also has a normal, expanded configuration as is shown in FIG. 1E. The prosthetic valve 10 includes a stent or stent frame 14, a valve structure 16 and a wrap 40 interconnected to the stent frame with a plurality of elongated members 54 (e.g., sutures, cords, wires, ribbons or the like). The stent frame 14 can assume any of the forms described above, and is generally constructed so as to be self-expandable from the compressed arrangement (FIG. 1D) to the normal, expanded delivery arrangement (FIG. 1E). In other embodiments, the stent frame 14 is expandable to the expanded arrangement by a separate device (e.g., a balloon internally located within the stent frame 14). The stent frame 14 is at least partially formed by a plurality of cells 18 defined by a plurality of segments 20 that are adjoined at nodes 22. The valve structure 16 is assembled to the stent frame 14 and provides two or more (typically three) leaflets 24. The valve structure 16 can assume any of the forms described above, and can be assembled to the stent frame 14 in various manners, such as by sewing the valve structure 16 to one or more of the segments 20 defined by the stent frame 14.

The prosthetic valve 10 FIGS. 1D-1E is configured for replacing an aortic valve (not shown). Alternatively, other shapes are also envisioned, adapted for the specific anatomy of the valve to be replaced (e.g., prosthetic valves in accordance with the present disclosure can alternatively be shaped and/or sized for replacing a native mitral, pulmonic, or tricuspid valve). Regardless, the valve structure 16 can be arranged to extend less than an entire length of the stent frame 14. In particular, the valve structure 16 can be assembled to, and extend along, a first end 26 of the prosthetic valve 10, whereas a second end 28 can be free of the valve structure 16 material. A wide variety of other constructions are also acceptable and within the scope of the present disclosure. For example, the valve structure 16 can be sized and shaped to extend along an entirety, or a near entirety, of a length of the stent frame 14.

In certain embodiments, expansion and contraction of the stent frame 14 is controlled with one or more sutures 12 actuated by the delivery device 1 as described above. The sutures 12 can be wrapped around the outer circumference of the stent frame 14. At the first and second ends 26, 28, for example, the compression sutures 12 can be woven through a plurality of eyelets 30, 32 provided in the stent frame 14 to provide for, with the assistance of the delivery device 1, compressing and releasing of the compressive tension placed on the stent frame 14. In addition, one or more sutures 12 can be positioned around the stent frame 14 between the first and second ends, 26, 28, to provide uniform compressing the stent frame 14.

The prosthetic valves disclosed herein include a paravalvular leakage mitigation and prevention wrap, such the wrap 40 of FIGS. 1B-1E. In some embodiments, during transcatheter, transfemoral or subclavian delivery, for example, of the prosthetic valve 10, the wrap 40 is positioned in front of (i.e. distal to) the stent frame 14. In the case of transapical delivery, the wrap is positioned behind (i.e. proximal to) the stent frame 14. Regardless of the distal or proximal placement of the wrap 40 with respect to the stent frame 14, the plurality of elongated members 54 interconnecting the wrap 40 to the stent frame 14 are arranged and configured so that upon expansion of the stent frame 14 from the compressed, delivery arrangement of FIGS. 1B and 1D to the expanded configuration of FIGS. 1C and 1E, the elongated members 54 automatically pull the wrap 40 proximally over and around the stent frame 14. In some embodiments, during delivery of the prosthetic valve 10, the wrap 40 is positioned at least partially around stent frame 14 and the elongated members 54 pull the rest of the wrap 40 over and around the stent frame 14. In some embodiments, during delivery of the prosthetic valve 10, the wrap 40 is completely positioned around stent frame 14 and the elongated members 54 change the configuration of the wrap 40 from a delivery configuration to a deployed configuration.

In some embodiments further discussed below, the wrap is pulled upwardly, inverting itself in the process. In some embodiments disclosed herein, the wrap generally comprises a cylindrical body of material having a secured end and a free end. In some embodiments, the wrap may comprises a portion of a cylindrical body of material or a non-cylindrical body of material having a secured end and a free end. The wrap material can be made of a flexible material such as polyester weave, velour, and tissue, for example. The wrap can have a diameter that is roughly the same as a diameter of the expanded stent frame. The wrap can also include edging on one or more of the free and secured ends. If edging is provided on the secured end, it can be used to connect the wrap to an internal skirt provided inside the stent frame, if provided (not shown).

Figure 2A:
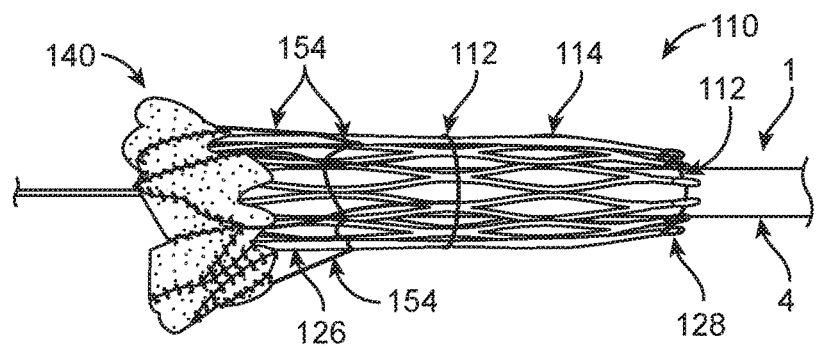
FIG. 2A is a front view of a stented prosthetic heart valve similar to that of FIGS. 1D-1E, the stented prosthetic heart valve secured over the delivery device in a compressed arrangement for delivery; wherein a wrap of the stented prosthetic heart valve extends beyond the stent frame (the delivery device is only partially shown and the valve leaflets are not shown for clarity).
Figure 2B:
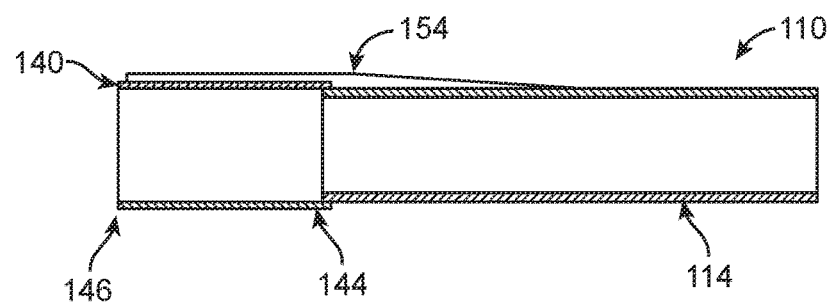
FIG. 2B is a partial, schematic illustration of the stented prosthetic heart valve and wrap of FIG. 2A in the compressed, delivery arrangement.

A prosthetic valve 110, as seen in FIGS. 2A-2G, can be delivered and deployed with the delivery device 1 in the manner as schematically illustrated and described with respect to FIGS. 1A-1E. The prosthetic valve 110 is generally identical to that illustrated and described with respect to FIGS. 1B-1E. The prosthetic valve 110 includes a wrap 140 that generally comprises a cylindrical body of material 142 having a secured end 144 and a free end 146. The secured end 144 of the wrap 140 can be secured to the stent frame 114 with one or more attachment sutures 152 threaded through the eyelets 130 of the stent frame 114. FIG. 2A illustrates the prosthetic valve 110 held in a compressed, delivery arrangement on a shaft 4 of the delivery device 1 (partially shown) with at least one compression suture 112. In the compressed or delivery arrangement, the wrap 140 extends from or beyond (i.e. distal to) the stent frame 114 so that the profile, or circumference, of the prosthetic valve 110 is not increased during delivery by the addition of the wrap 140. It is highly desirable that the profile of the prosthetic valve 110 be as small as possible to facilitate transcatheter delivery of the prosthetic valve 110.

Figure 2C:
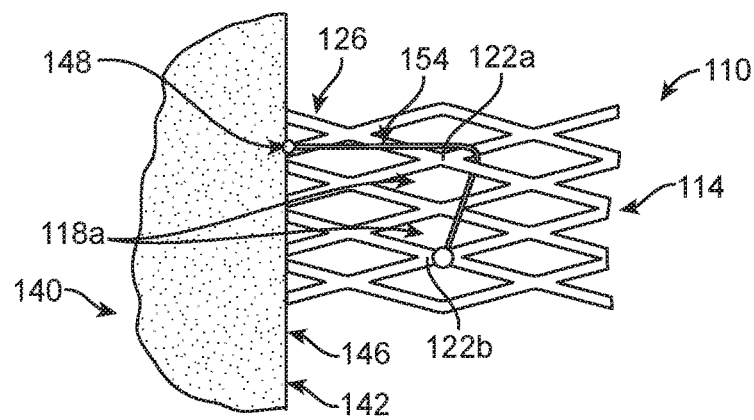
FIG. 2C is a partial, schematic illustration of the stented prosthetic heart valve of FIG. 2A-2B illustrating a representative elongated member interconnecting the wrap to the stent frame.
Figure 2D:
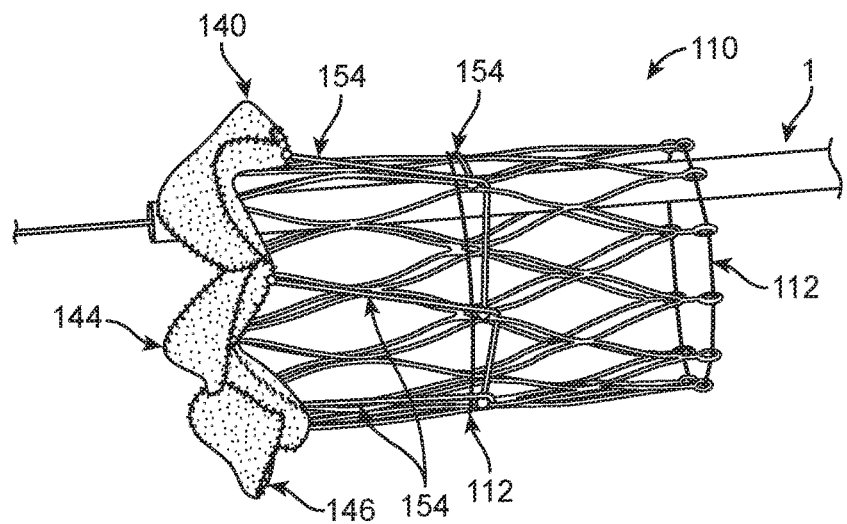
FIG. 2D is a front view of the stented prosthetic heart valve of FIGS. 2A-2C in a partially deployed arrangement; wherein the stent frame is partially expanded and the elongated members attached thereto have started to pull the wrap over and onto the stent frame.
Figure 2E:
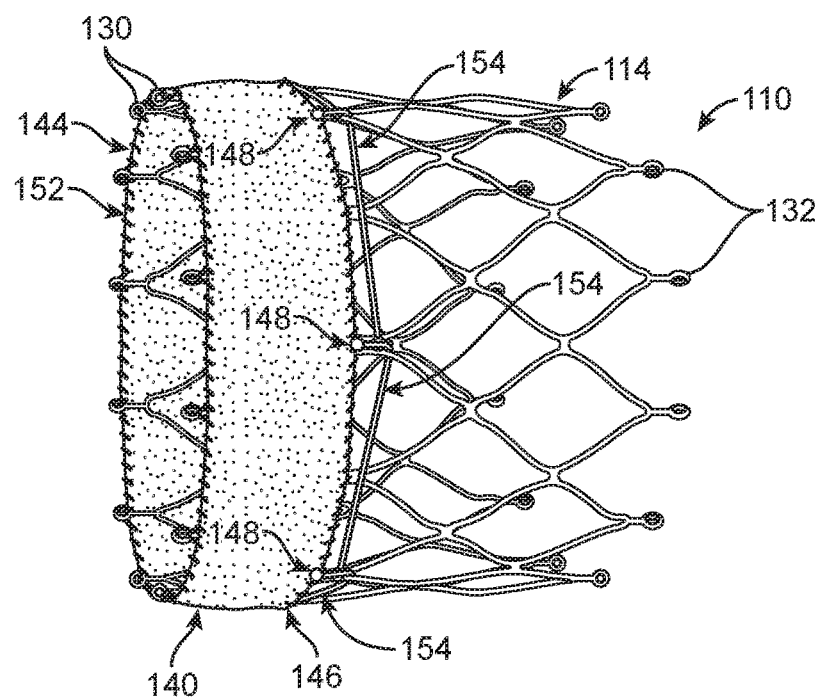
FIG. 2E is a perspective view of the stented prosthetic heart valve of FIGS. 2A-2D in a deployed arrangement; wherein the stented prosthetic heart valve is released from the delivery device and the wrap is secured over the stent frame.
Figure 2F:
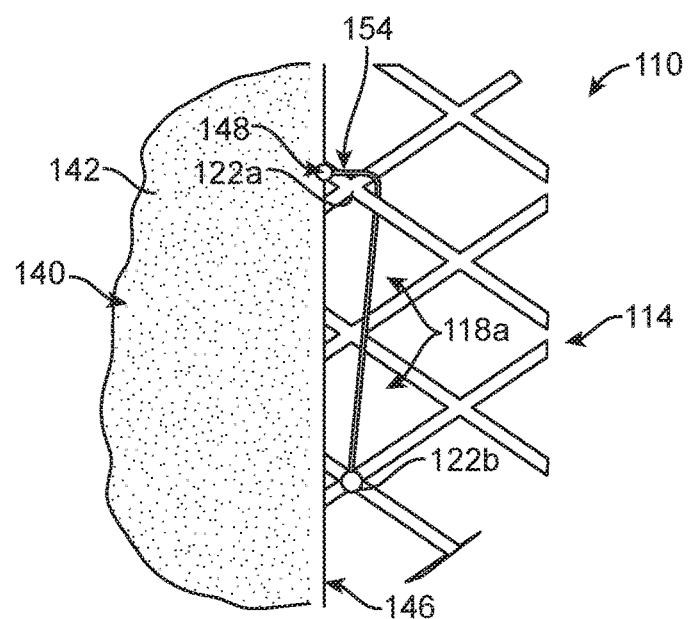
FIG. 2F is a partial, schematic illustration of the stented prosthetic heart valve and wrap of FIGS. 2A-2E in the deployed arrangement.
Figure 2G:
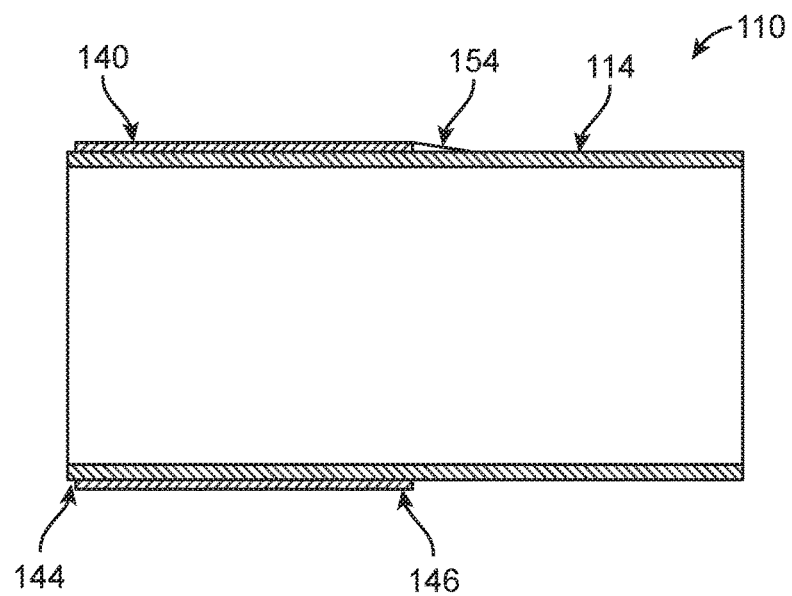
FIG. 2G is a partial, schematic illustration of the stented prosthetic heart valve of FIGS. 2A-2F in the deployed arrangement (only one elongated member is shown for clarity).

As best shown in FIGS. 2C and 2F, to fully deploy the wrap 140, a plurality of elongated members 154 are provided, which are configured to automatically pull the wrap 140 into position upon expansion of the prosthetic valve 110 during deployment. The elongated members 154 can be sutures, cords, wires, ribbons or the like. In the illustrated embodiment, the wrap 140 is actuated with six elongated members 154 equally spaced around the stent frame 114 and attached proximate the free end 146 of the wrap 140 (not all of the elongated members 154 are visible, more or less elongated members can alternatively be utilized). The wrap 140 can optionally include openings 148 in which the attachment and elongated members 154 are secured or pass through as will be further discussed below. As is generally illustrated in FIGS. 2C and 2F (only one exemplary elongated member 154 is illustrated), each elongated member 154 extends from the free end 146 and is wrapped around an immediately adjacent pivot node 122a of the stent frame 114, then the elongated member 154 is woven across two cells 118a of the stent frame 114 to a second node 122b to which the respective elongated member 154 is attached. This "two-cell" threading arrangement provides a sufficient amount of slack in the respective elongated member 154 to allow the wrap 140 to be positioned proximal to the stent frame 114 when the stent frame 114 is in the compressed, delivery configuration, as is illustrated in FIG. 2A. It will be understood that the number of cells 118a in which the elongated member 154 spans can vary based on the stent frame 114 design. The elongated members 154 are woven and configured to provide a length of travel required to pull the wrap 140 from the delivery arrangement to the deployed arrangement. When the stent frame 114 is allowed to expand by releasing tension in the compression sutures 112 or otherwise, each elongated member 154 is pulled across the expanding exterior circumference of the stent frame 114, thus also pulling the wrap 140 proximally into position over the stent frame 114 as is shown in FIGS. 2B-2G. In other words, as the stent frame 114 expands, the elongated members 154 pull the free end 146 of the wrap 140 until the free end 146 flips over the secured end 144 and the free end 146 is proximal to the secured end 144 in the deployed arrangement. The expansion of the stent frame 114, and thus, the corresponding deployment of the wrap 140 can be controlled and adjusted, as needed, by either increasing or decreasing the tension in the compression suture(s) 112 with delivery device 1.

Figure 3A:
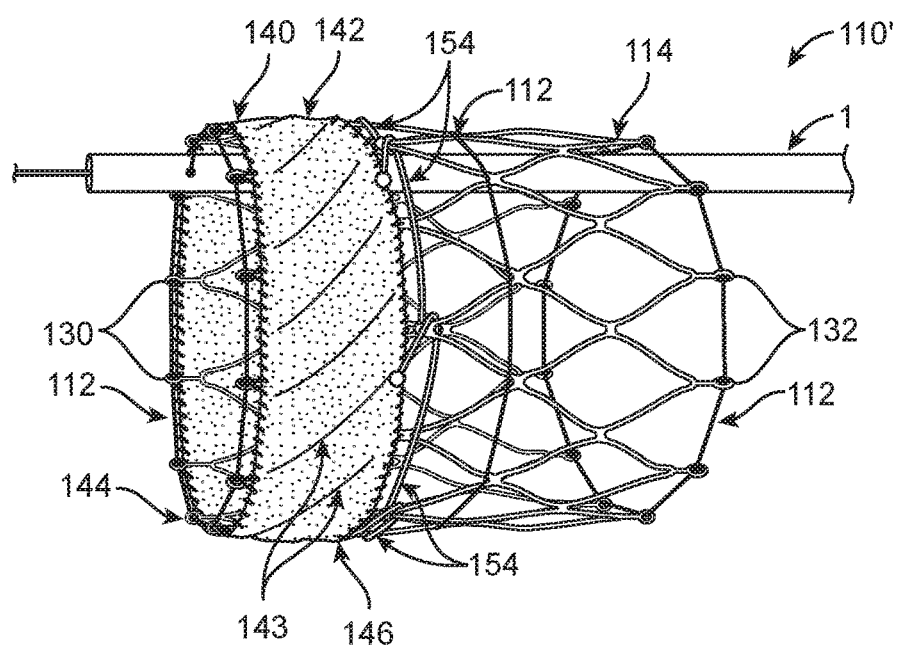
FIG. 3A is a perspective view of a stented prosthetic heart valve having a stent frame having a wrap secured over the delivery device in an expanded, deployed arrangement (the delivery device is only partially shown and the valve leaflets are not shown for clarity).
Figure 3B:
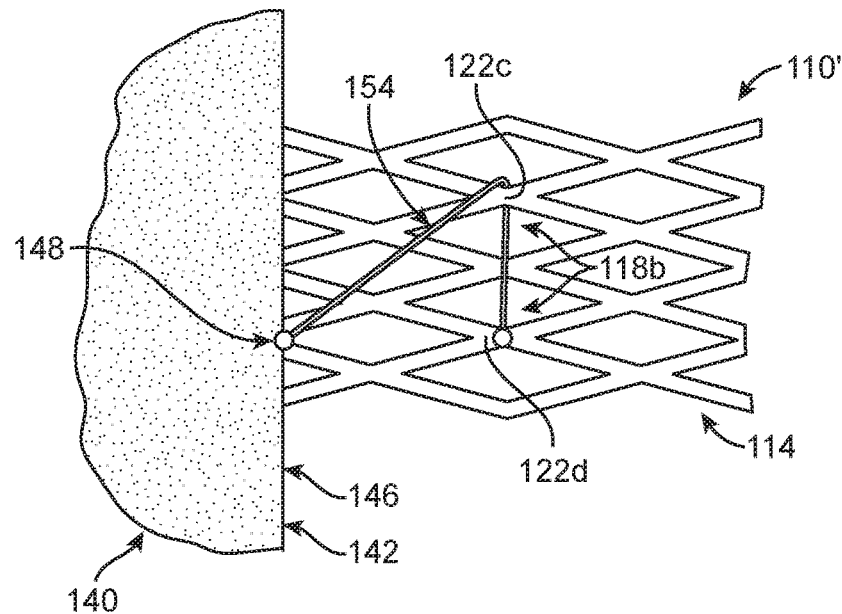
FIG. 3B is a schematic illustration of the wrap of the stented prosthetic heart valve of FIG. 3A in the delivery arrangement illustrating how one representative elongated member is secured in an offset manner to two cells of the stent frame.
Figure 3C:
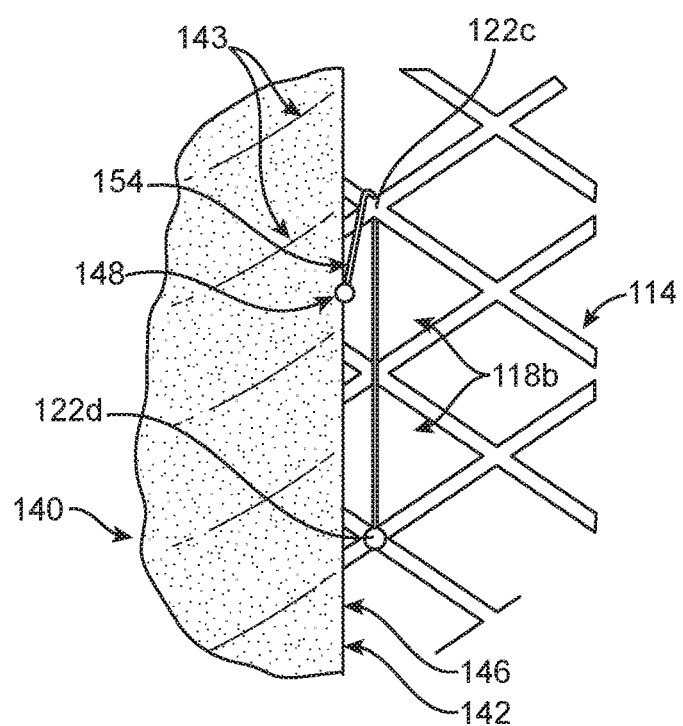
FIG. 3C is a schematic illustration of the wrap of FIGS. 3A-3B when the stented prosthetic heart valve of FIG. 3A in an expanded arrangement.

An alternate prosthetic valve 110', which is generally illustrated in FIGS. 3A-3C, is almost identical to that of FIGS. 2A-2G with the exception that each elongated member 154 is woven to be offset to provide a greater suture length, which may be required for wider wrap configurations requiring that a second or free end 146 of the wrap 140 be pulled a greater distance from the delivery arrangement (FIG. 3B) to the deployment arrangement (FIGS. 3A and 3C). Having the elongated members 154 woven in a way in which they are offset also results in rippling and ridges 143 in the wrap body material 142 that is believed to help fill gaps around the stent frame 114 to further prevent any potential paravalvular leakage. As illustrated, each elongated member 154 extends from a free end 146 of the wrap 140 and to an adjacent node 122c opposite the direction of the node 122d on which the elongated member 154 is ultimately attached, two cells 118b away. As generally illustrated in FIGS. 3B-3C, as viewed from the first end 126, the respective elongated member 154 extends clockwise to and wraps around adjacent pivot node 122c and then counterclockwise back across a width of two or more cells 118b to the next node 122d to which the elongated member 154 is secured by tying or the like. As will be understood, although not illustrated, each elongated member 154 can alternatively extend counterclockwise to and wrap around an adjacent pivot node and then clockwise back across a width of two or more cells to the next node to which the elongated member is secured. As with the prior disclosed embodiments, a valve structure of the prosthetic valve 110' is not illustrated in the figures for clarity.

Figure 4A:
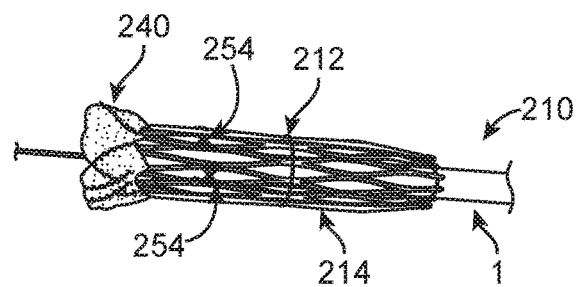
FIG. 4A is a front view of a stented prosthetic heart valve having a stent frame secured over the delivery device (the delivery device is only partially shown and the valve leaflets are not shown for clarity); the stented prosthetic heart valve having a wrap extends beyond the stent frame in a delivery arrangement.
Figure 4B:
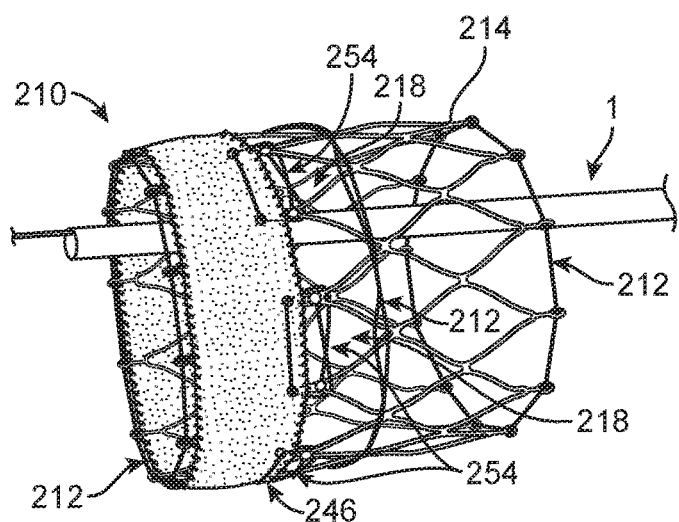
FIG. 4B is a perspective view of the stented prosthetic heart valve of FIG. 4A in an expanded, deployed arrangement prior to releasing the stented prosthetic heart valve from the delivery device.
Figure 4C:
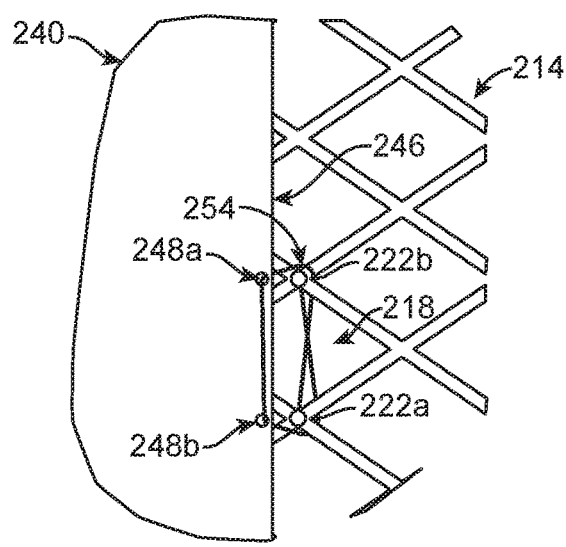
FIG. 4C is a schematic illustration of the stented prosthetic heart valve of FIGS. 4A-4B illustrating how one representative elongated member can be secured to one of a plurality of cells of the stent frame.

A further prosthetic valve 210 is illustrated in FIGS. 4A-4C. In this embodiment, which is largely similar to those disclosed above, there are a plurality of (e.g. six) elongated members 254 equidistantly spaced around and secured to a free end 246 of a wrap 240 (not all of the elongated members are visible). Instead of the elongated members 254 extending across two or more cells 218 of the stent frame 214, as in prior embodiments, the elongated members 254 are each woven around one respective cell 218 (i.e. "one-cell" threading). As best illustrated in FIG. 4C illustrating the threading of one representative elongated member 254, each elongated member 254 extends from a first node 222a to which the elongated member 254 is attached. The respective elongated member 254 then is threaded across an adjacent cell 218 to a second node 222b around which the respective elongated member 254 is wound. The respective elongated member 254 is then directed toward the free end 246 of the wrap 240, which includes a first hole 248a, through which the elongated member 254 is threaded. The respective elongated member 254 is then threaded back in the direction of the first node 222a to a second hole 248b in the free end 246 and then up to and around the adjacent first node 222a. The elongated member 254 is then threaded back across the cell 218 to the second node 222b, to which the respective elongated member 254 is secured by tying or the like. The remaining five elongated members 254 (not all of which are visible) can be threaded in a similar fashion. Similar to prior embodiments, when the stent frame 214 is allowed to expand via releasing tension in one or more compression sutures 212 or otherwise, each elongated member 254 will be pulled across the exterior circumference of the stent frame 214, thus also pulling the wrap 240 into position from the delivery arrangement of FIG. 4A to the deployed arrangement of FIGS. 4B-4C. As with the prior disclosed embodiments, the elongated members 254 can be of the type disclosed above and a valve structure is not illustrated in the figures for clarity.

Figure 5A:
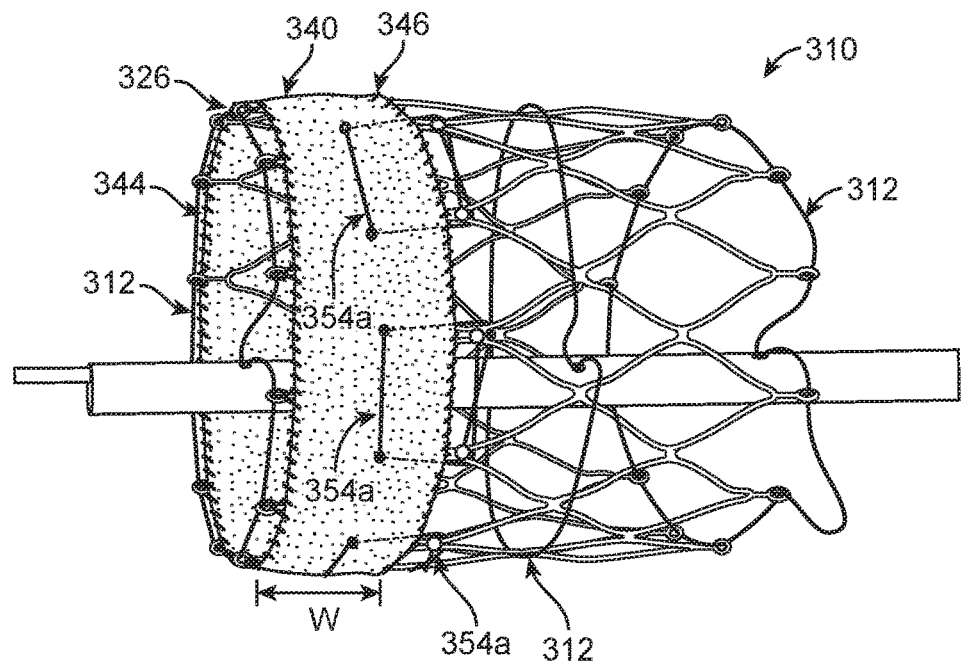
FIG. 5A is a perspective view of a partially assembled stented prosthetic heart valve having a wrap; the stented prosthetic heart valve further having a stent frame secured over the delivery device (the delivery device is only partially shown and the valve leaflets are not shown for clarity).
Figure 5B:
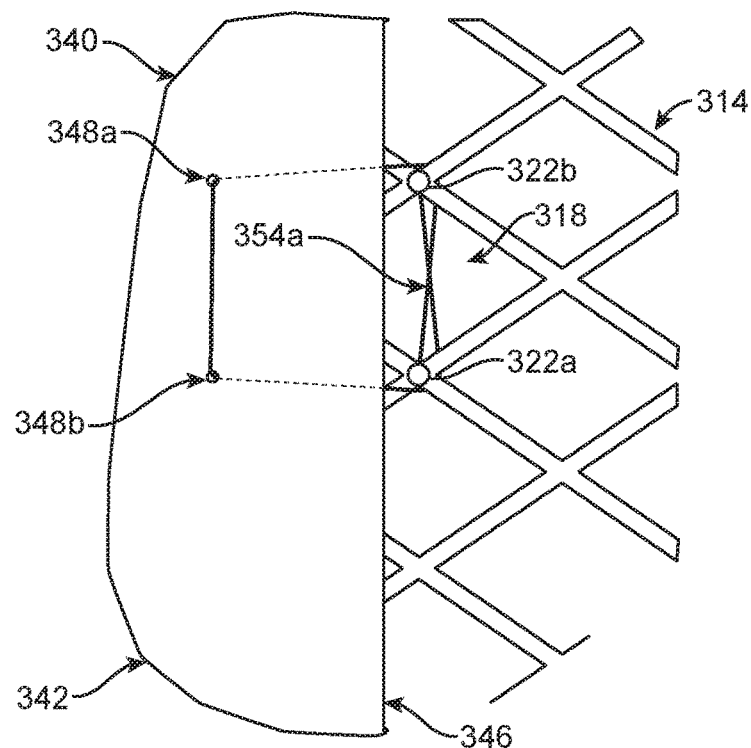
FIG. 5B is a schematic illustration of the stented prosthetic heart valve of FIG. 5A illustrating how one representative elongated member is secured to one of a plurality of cells of the stent frame.
Figure 5C:
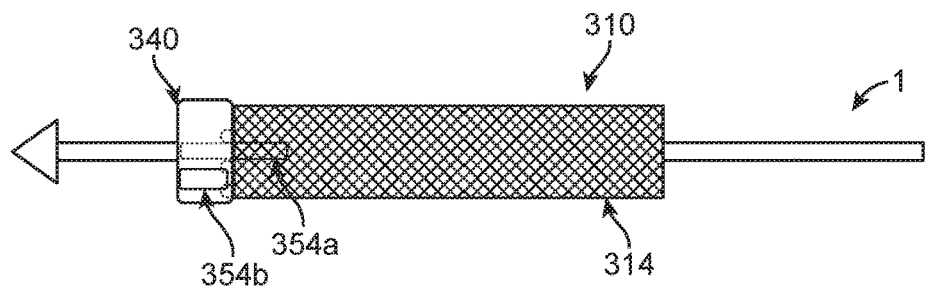
FIG. 5C is a schematic illustration of the stented prosthetic heart valve of FIGS. 5A-5B with the stented prosthetic heart valve and the wrap loaded onto the delivery device (only part of which is shown).
Figure 5D:
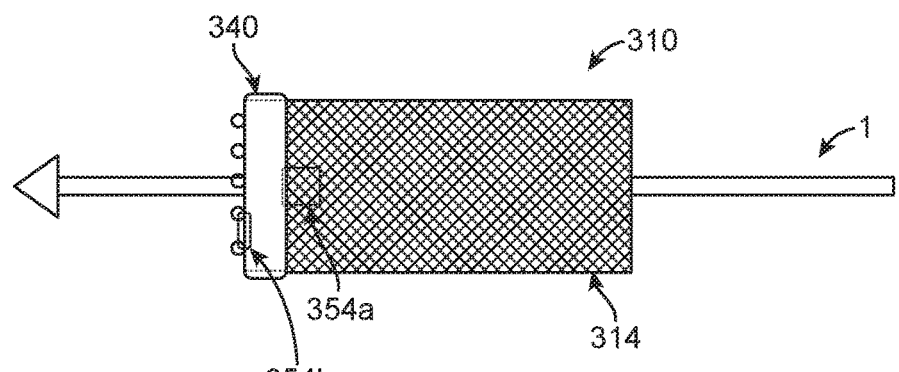
FIG. 5D is a schematic illustration of the stented prosthetic heart valve of FIGS. 5A-5C with the stented prosthetic heart valve in an expanded, deployed arrangement, which automatically positions the wrap over and onto the stent frame.
Figure 5E:
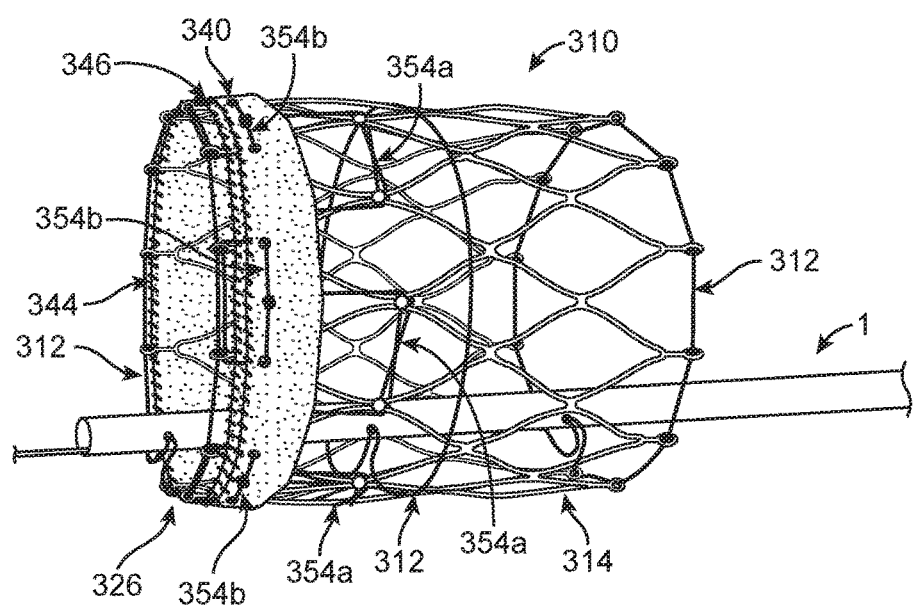
FIG. 5E is a perspective view of the stented prosthetic heart valve of FIGS. 5A-5D illustrating the stented prosthetic heart valve in an expanded, deployed arrangement; wherein the wrap is folded over itself onto the stent frame.

Another prosthetic valve 310 is generally illustrated in FIGS. 5A-5E. In this embodiment, the prosthetic valve 310 includes a wrap 340 and a plurality of elongated members 354a equally spaced around a circumference of the wrap 340 that are woven approximately midway through a width W of the wrap 340. FIGS. 5A and 5B are pre-assembly views illustrating the prosthetic valve 310 prior to the attachment of elongated members 354b and placement of the wrap 340 adjacent a stent frame 314 of the prosthetic valve 310 for delivery (see also, FIGS. 5C-5E). To finalize the assembly of the wrap 340, secondary elongated members 354b are woven through the distal end 326 of the stent frame 314 and a free end 346 of the wrap 340 and tied to form a closed loop (see, e.g. FIG. 5E). When the stent frame 314 expands, the wrap 340 transitions from a delivery arrangement of FIG. 5C to a deployed arrangement of FIGS. 5D and 5E. As the stent frame 314 expands due to the release of compressive tension provided by compression sutures 312 actuated by delivery device 1, the wrap 340 is pulled in such a way that the wrap 340 folds over the stent frame 314 and over itself at the elongated member 354a such that the free end 346 and a secured end 344 of the wrap 340 are in approximate alignment with each other at a first end 326 of the stent frame 314 as is generally illustrated in FIG. 5E. This embodiment provides for a thicker wrap 340 once deployed, but does not add to the prosthetic valve 310 profile during delivery. A thicker wrap 340 in the deployed arrangement is believed to provide extra sealing capabilities to prevent paravalvular leakage as compared to the embodiments disclosed above. In this embodiment, there are two layers of wrap body material 342 surrounding the first end 326 of the stent frame 314, wherein the secured end 344 is approximately even with the free end 346 in the deployed arrangement. As is best illustrated in FIG. 5B, each elongated member 354a is tied to a first node 322a and it is threaded across one cell 318 to a second node 322b around which the elongated member 354a is wound. The elongated member 354 then extends down through a hole 348a approximately midway through the wrap 340. Then the elongated member 354 extends over to a second hole 348b in the wrap 340 and then up toward the first node 322a. Except as explicitly stated, the wrap 340 and elongated members 354 can be of the type as described with respect to the embodiments above. As with the prior disclosed embodiments, a valve structure is not illustrated in the figures for clarity.

Figure 6A:
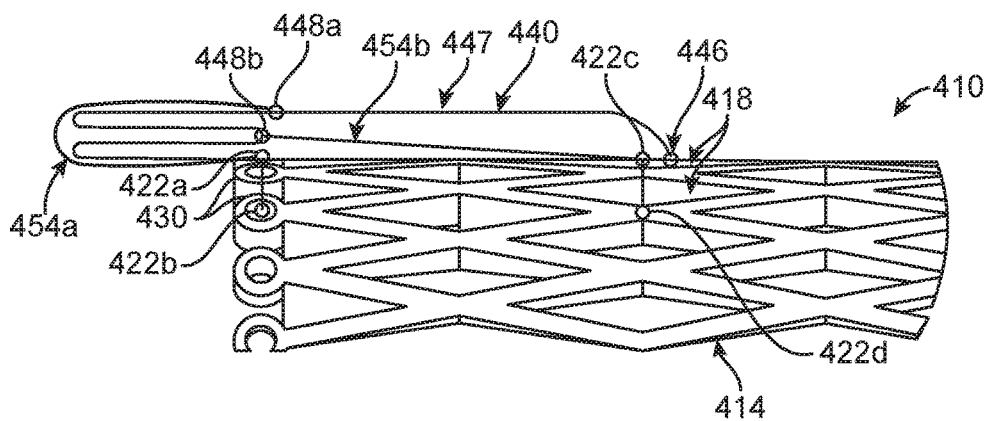
FIG. 6A is a partial, schematic illustration of another embodiment of a stented prosthetic heart valve having a wrap secured to a stent frame with a plurality of elongated members, the stented prosthetic heart valve in a compressed, delivery arrangement and the wrap extending beyond the stent frame (valve leaflets of the stented prosthetic heart valve are not shown for clarity).
Figure 6B:
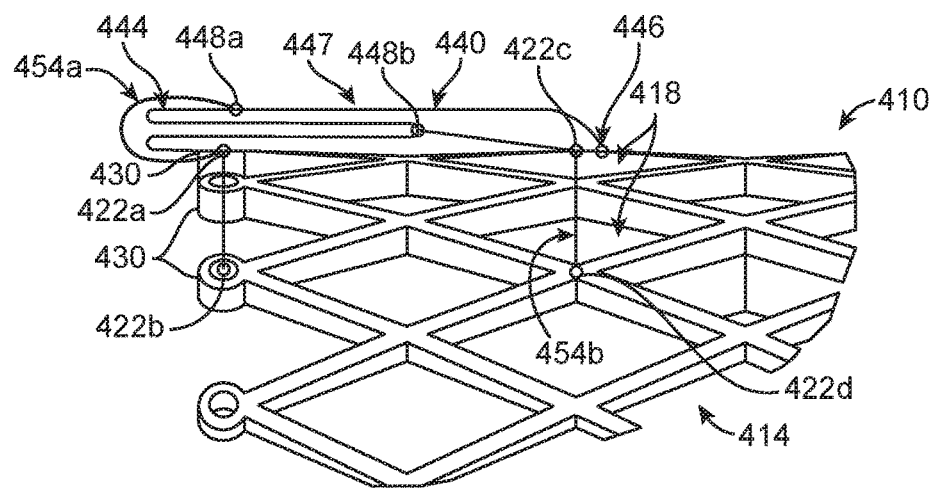
FIG. 6B is a partial, schematic illustration of the stented prosthetic heart valve of FIG. 6A in a transitory position in between the compressed, delivery arrangement and an expanded, deployed arrangement.
Figure 6C:
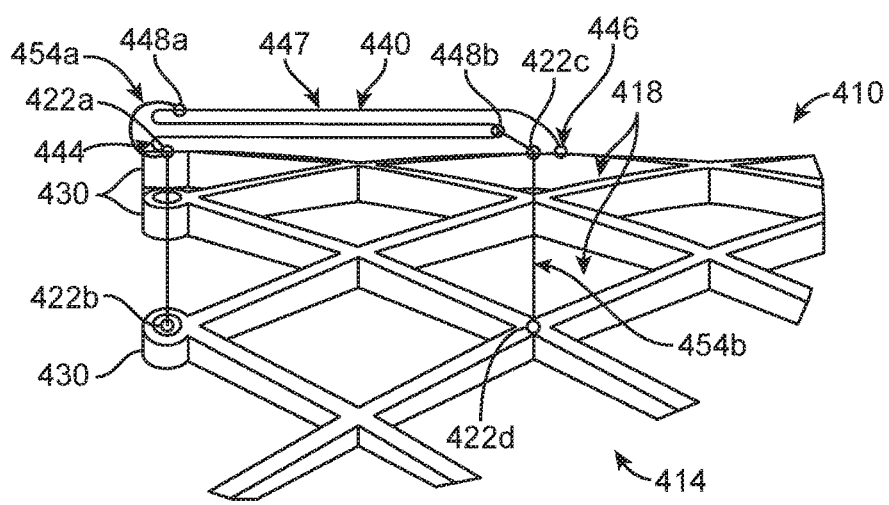
FIG. 6C is a partial, schematic illustration of the stented prosthetic heart valve of FIGS. 6A-6B in the expanded, deployed arrangement; wherein the wrap is positioned over the stent frame.

FIGS. 6A-6C schematically illustrate portions of yet an additional prosthetic valve 410 (partially shown) having an inverting wrap 440 secured to a stent frame 414 (also partially shown). As with the prior disclosed embodiments, the valve leaflets, as shown in FIGS. 1D and 1E, are not shown in FIGS. 6A-6C for clarity. The wrap 440 includes a proximal end 446, a distal end 444 and midsection 447 therebetween. In this embodiment, the proximal end 446 is most proximal with respect to the stent frame 414 and is secured to the stent frame 414 with attachment sutures (not visible) or the like. The distal end 444 is positioned distally as compared to the proximal end 446. The wrap 440 is also secured to the stent frame 414 at two points 448a, 448b within the midsection 447 with a plurality of elongated member pairs (only one elongated member pair 454a, 454b is shown in FIGS. 6A-6C). Each elongated member pair includes two elongated members 454a, 454b, which can be woven around the stent frame 414 in any fashion disclosed herein. Various embodiments can include a plurality (e.g. six) elongated members 454a, 454b similarly threaded and spaced equally around the stent frame 414. The elongated members 454a, 454b can be of the type as disclosed with prior embodiments.

In one exemplary method of threading one pair of elongated members 454a, 454b illustrated in FIGS. 6A-6C, the first elongated member 454a can be tied or otherwise secured to a point 448a in the midsection 447 of the wrap 440 and then directed to a pivot point 422a at an eyelet 430 or other portion of the stent frame 414 through which the first elongated member 454a can be threaded through or around. The first elongated member 454a is then threaded to a second point 422b at the stent frame 414 that is two cells 418 away. At the second point 422b on the stent frame 414, which can be an eyelet 430, the first elongated member 454a is secured via tying or the like. The second elongated member 454b is attached at a point 448b in the midsection 477 of the wrap 440 and extends proximally to pivot node 422c in stent frame 414 around which the second elongated member 454b is threaded and directed to a second node 422d of the stent frame 414 that is two cells 418 away at which the second elongated member 454b is secured by tying or the like. In one embodiment, the approximate distance from pivot node 422c to the pivot point 422a from the proximal end 446 is approximately one third of a width of the wrap 440. In a further embodiment, the point 448b is approximately equal distance from 448a as is from the proximal end 446, which is approximately one third of a width of the wrap 440. As with prior disclosed embodiments, when the stent frame 414 expands from the delivery arrangement (FIG. 6A) to the deployed arrangement (FIG. 6C), the expansion of the stent frame 414 correspondingly draws the elongated members 454a, 454b, thus pulling the midsection 447 of the wrap 440 toward the proximal end 446 of the wrap 440 so that the wrap 440 becomes inverted and has a triple thickness along a least part of the wrap 440 (see, in particular, FIG. 6C). This embodiment is also particularly useful in preventing a "parachute effect," which may be observed in prior disclosed embodiments where the wrap is drawn up and over the stent frame, which can collect blood and make it more difficult to flip the wrap from the delivery arrangement to the deployed arrangement.

Figure 7A:
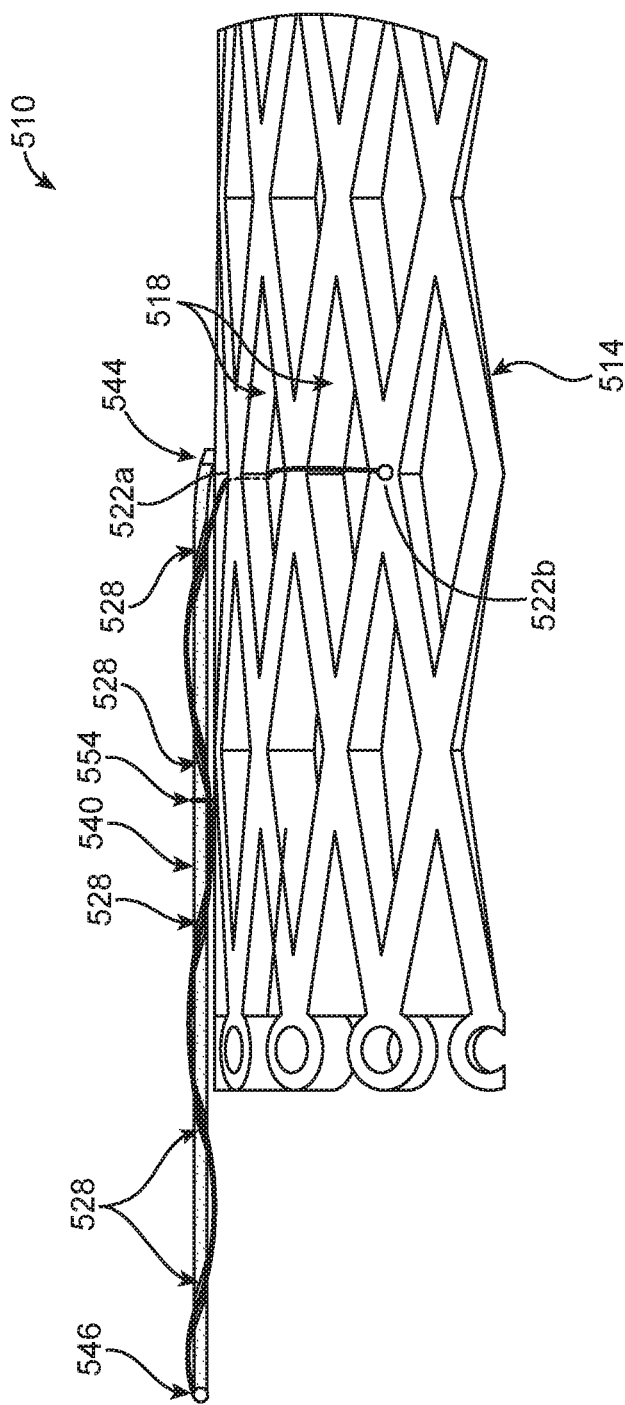
FIG. 7A is a partial, schematic illustration of another embodiment of a stented prosthetic heart valve having a wrap secured to a stent frame with a plurality of elongated members, the stented prosthetic heart valve in a compressed, delivery arrangement and the wrap extending beyond the stent frame (valve leaflets of the stented prosthetic heart valve are not shown for clarity).
Figure 7B:
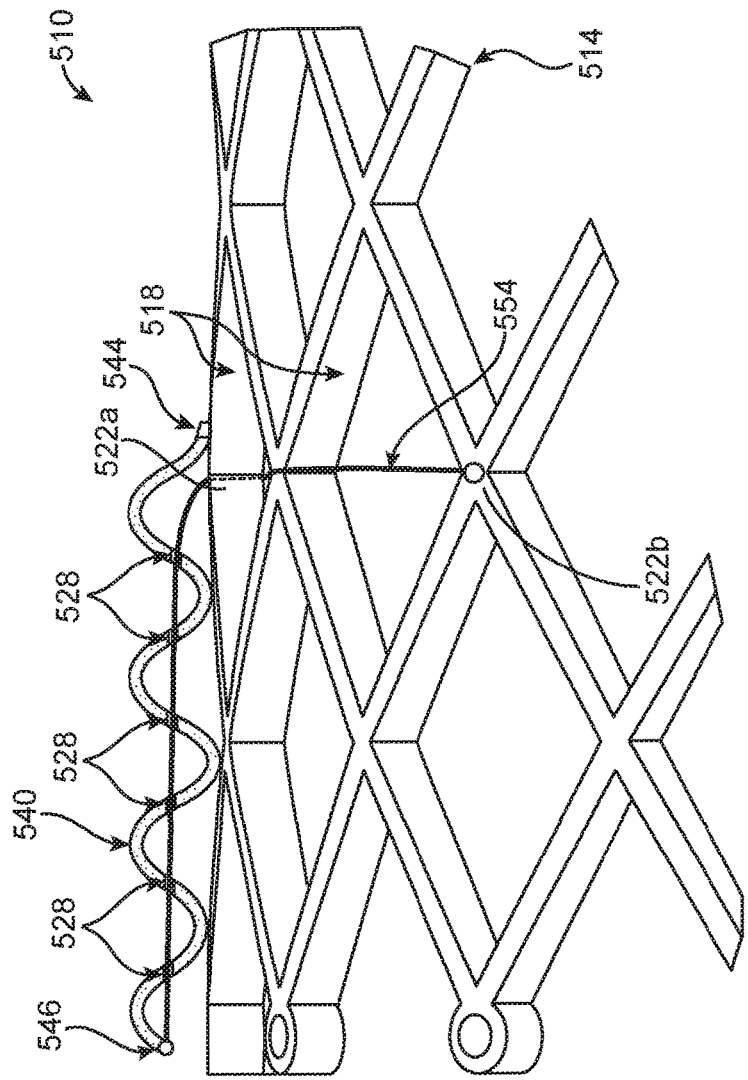
FIG. 7B is a partial, schematic illustration of the stented prosthetic heart valve of FIG. 7A in the expanded, deployed arrangement; wherein the wrap is positioned over the stent frame.

As generally illustrated in FIGS. 7A-7B, a prosthetic valve 510 (partially shown) is generally identical to the prosthetic valve 10 and can be delivered and deployed with the delivery device 1 in the manner as schematically illustrated and described with respect to FIGS. 1A-1E. The prosthetic valve 510 includes a wrap 540 that generally comprises a cylindrical body of material having a secured end 544 and a free end 546. The secured end 544 of the wrap 540 is secured to the stent frame 514. FIG. 7A generally depicts the prosthetic valve 510 held in a compressed, delivery arrangement. To fully deploy the wrap 540, a plurality of elongated members 554 are provided, which are configured to automatically pull the wrap 540 into position upon expansion of the prosthetic valve 510 during deployment (only one demonstrative elongated member 554 is shown for ease of illustration). The plurality of elongated members 554 can be equally spaced around the stent frame 514 and attached proximate the free end 546 of the wrap 540. Each elongated member 554 extends from the free end 546, through apertures 528 in the wrap and extends to the stent frame 514 where it is wrapped around a pivot node 522a of the stent frame 514, then the elongated member 554 is woven across two adjacent cells 518 of the stent frame 514 to a second node 522b to which the respective elongated member 554 is attached. This "two-cell" threading arrangement provides a sufficient amount of slack in the respective elongated member 554 to allow the wrap 540 to be positioned sufficiently proximal to the stent frame 514 when the stent frame 514 is in the compressed, delivery configuration, as is illustrated in FIG. 7A. It will be understood that the number of cells 518 in which the elongated member 554 spans can vary based on the stent frame 514 design. The elongated members 554 are woven and configured to provide a length of travel required to pull the wrap 540 from the delivery arrangement to the deployed arrangement. When the stent frame 514 expands for deployment, each elongated member 554 is pulled across the expanding exterior circumference of the stent frame 514, thus also pulling the free end 546 of the wrap 540 proximally into position over the stent frame 514 as is shown in FIG. 7B.

Figure 8B:
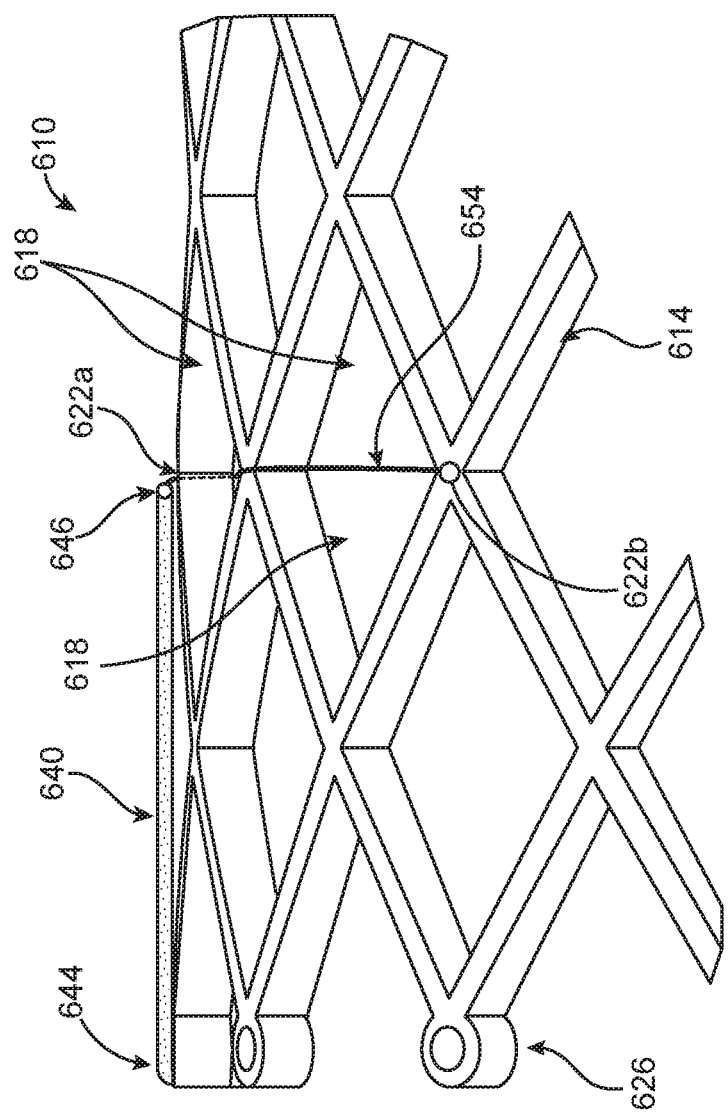
FIG. 8B is a partial, schematic illustration of the stented prosthetic heart valve of FIG. 8A in the expanded, deployed arrangement; wherein the wrap is positioned over the stent frame.

Similarly, a prosthetic valve 610 of FIGS. 8A-8B (partially shown) is generally identical to the prosthetic valve 10 and can be delivered and deployed with the delivery device 1 in the manner as schematically illustrated and described with respect to FIGS. 1A-1E. The prosthetic valve 610 includes a wrap 640 that generally comprises a cylindrical body of material having a secured end 644 and a free end 646. The secured end 644 of the wrap 640 can be secured to the stent frame 614. FIG. 8A generally depicts the prosthetic valve 610 held in a compressed, delivery arrangement. To fully deploy the wrap 640, a plurality of elongated members 654 are provided, which are configured to automatically pull the wrap 640 into position upon expansion of the prosthetic valve 610 during deployment (only one demonstrative elongated member 654 is shown for ease of illustration). The plurality of elongated members 654 can be equally spaced around the stent frame 614 and attached proximate the free end 646 of the wrap 640. Each elongated member 654 extends from the free end 646 and extends to the stent frame 614 where it is wrapped around a pivot node 622a of the stent frame 614, then the elongated member 654 is woven across two adjacent cells 618 of the stent frame 614 to a second node 622b to which the respective elongated member 654 is attached. This "two-cell" threading arrangement provides a sufficient amount of slack in the respective elongated member 654 to allow the wrap 640 to be positioned sufficiently proximal to the stent frame 614 when the stent frame 614 is in the compressed, delivery configuration, as is illustrated in FIG. 8A. It will be understood that the number of cells 618 in which the elongated member 654 spans can vary based on the stent frame 614 design. The elongated members 654 are woven and configured to provide a length of travel required to pull the wrap 640 from the delivery arrangement to the deployed arrangement. When the stent frame 614 expands for deployment, each elongated member 654 is pulled across the expanding exterior circumference of the stent frame 614, thus also pulling the free end 646 of the wrap 640 proximally into position over the stent frame 614 as is shown in FIG. 8B.

In view of the present disclosure, it will be understood that there are many ways in which the elongated members can be threaded and arranged around the stent frame to provide a configuration in which the elongated members do not cross or contact each other, while still providing a plurality of elongated members to actuate transition of the wrap from a delivery arrangement to a deployment arrangement. Such embodiments provide for many points of attachment to ease actuation or flipping of the wrap, which movement is typically resisted by the patient's tissue. It will be further understood, in view of the teachings herein, the direction in which the elongated members are wrapped around the stent frame can be clockwise, counterclockwise or a combination thereof. Additional configurations embodying this concept are intended to be within the scope of the present disclosure.

Various sutures disclosed herein can be of many types commonly used for compressing stented prosthetic heart valves during delivery. In various embodiments, the elongated members can be elastic so that the wrap reaches its full deployed arrangement before the stent frame is in the full expanded deployed arrangement.

Although the present disclosure has been described with reference to preferred embodiments, workers skilled in the art will recognize that changes can be made in form and detail without departing from the spirit and scope of the present disclosure.

What is claimed is:

1. A stented prosthetic heart valve comprising:
a stent frame including a plurality of cells formed by segments adjoined at a plurality of nodes; the stent frame further including a first frame end and a second frame end;
a plurality of valve leaflets positioned within the stent frame; and
a wrap connected to the stent frame with at least one elongated member; each elongated member having two ends; wherein at least one end of the elongated member is secured to the stent frame; wherein the wrap has a delivery arrangement and a deployed arrangement that is actuated by expansion of the stent frame; wherein each elongated member extends from the wrap in a first direction, wraps around one respective node and then extends in a second direction that is different than the first direction.

2. The stented prosthetic heart valve of claim 1, wherein the stent frame defines a length and the wrap covers a greater portion of the length of the stent frame in the deployment arrangement as compared to the delivery arrangement.

3. The stented prosthetic heart valve of claim 1, wherein the wrap has first and second ends; wherein the second end of the wrap extends beyond the first frame end in the delivery arrangement and the second end of the wrap extends over the stent frame in the deployed arrangement.

4. The stented prosthetic heart valve of claim 3, wherein the first end of the wrap extends beyond the first frame end in the delivery arrangement the first end of the wrap extends over the stent frame in the deployed arrangement.

5. The stented prosthetic heart valve of claim 1, further comprising a plurality of elongated members connecting the stent frame and the wrap.

6. The stented prosthetic heart valve of claim 5, wherein the plurality of elongated members are arranged and configured so that they do not cross one another.

7. The stented prosthetic heart valve of claim 5, wherein the wrap has first and second ends; wherein six or more individual elongated members connect one of the first and second ends to the stent frame.

8. The stented prosthetic heart valve of claim 5, wherein the plurality of elongated members are arranged and configured to be offset such that in the deployed arrangement, a plurality of ridges are formed in an outwardly facing surface of the wrap.

9. The stented prosthetic heart valve of claim 5, wherein each elongated member is threaded around a single respective one of the plurality of cells.

10. The stented prosthetic heart valve of claim 1, wherein the two ends of the elongated member are connected to the stent frame.

11. The stented prosthetic heart valve of claim 1, further comprising a plurality of eyelets at the first frame end, wherein at least one of the plurality of elongated members is threaded through one of the eyelets.

12. The stented prosthetic heart valve of claim 1, wherein the wrap is folded over itself in the delivery arrangement.

13. The stented prosthetic heart valve of claim 12, wherein the wrap is not folded over itself in the deployed arrangement.

14. The stented prosthetic heart valve of claim 1, wherein in the deployed arrangement, each elongated member is oriented tangential to the stent frame.

15. The stented prosthetic heart valve of claim 1, wherein a longitudinal position of the wrap with respect to the stent frame varies in the delivery arrangement as compared to the deployment arrangement.

16. A stented prosthetic heart valve comprising:
a stent frame including a plurality of cells formed by segments adjoined at a plurality of nodes; the stent frame further including a first frame end and a second frame end;
a plurality of valve leaflets positioned within the stent frame; and
a wrap connected to the stent frame with a plurality of elongated members; each elongated member having two ends; wherein at least one end of the elongated member is secured to the stent frame; wherein the wrap has a delivery frame; wherein each elongated member is threaded around two respective cells of the plurality of cells; wherein each of the plurality of elongated members are not threaded around any of the respective cells around which another of the plurality of elongated members is threaded.

17. A stented prosthetic heart valve comprising:
a stent frame including a plurality of cells formed by segments adjoined at a plurality of nodes; the stent frame further including a first frame end and a second frame end;
a plurality of valve leaflets positioned within the stent frame; and
a wrap connected to the stent frame with a plurality of elongated members; each elongated member having two ends; wherein at least one end of the elongated member is secured to the stent frame; wherein the wrap has a delivery arrangement and a deployed arrangement that is actuated by expansion of the stent frame; wherein the wrap has first and seconds ends; wherein the first end of the wrap is secured to the stent frame and the second end of the wrap is movably connected to the stent frame with the plurality of elongated members; wherein each of the plurality of elongate members are threaded through the wrap approximately halfway between the first and second ends of the wrap.

18. The stented prosthetic heart valve of claim 17, wherein, in the deployed arrangement, the first and second ends are adjacent one another.

19. A stented prosthetic heart valve comprising:
a stent frame including a plurality of cells formed by segments adjoined at a plurality of nodes; the stent frame further including a first frame end and a second frame end;
a plurality of valve leaflets positioned within the stent frame; and
a wrap connected to the stent frame with a plurality of elongated members; each elongated member having two ends; wherein at least one end of the elongated member is secured to the stent frame; wherein the wrap has a delivery arrangement and a deployed arrangement that is actuated by expansion of the stent frame; wherein at least one elongated member extends between two adjacent nodes twice.

20. A stented prosthetic heart valve comprising:
a stent frame including a plurality of cells formed by segments adjoined at a plurality of nodes; the stent frame further including a first frame end and a second frame end;

a plurality of valve leaflets positioned within the stent frame; and a wrap connected to the stent frame with at least one elongated member; each elongated member having two ends; wherein at least one end of the elongated member is secured to the stent frame; wherein the wrap has a delivery arrangement and a deployed arrangement that is actuated by expansion of the stent frame; wherein the wrap has first and second ends;

wherein the wrap has a midsection between the first end of the wrap and the second end of the wrap; wherein, in the deployed arrangement, the wrap is folded at the midsection.

21. The stented prosthetic heart valve of claim 20, wherein the midsection of the wrap is closer to the first frame end when in the deployed arrangement as compared to the delivery arrangement.

22. The stented prosthetic heart valve of claim 20, wherein the midsection of the wrap is connected to the stent frame such that each elongated member slidably wraps around one node and then horizontally across a width of at least one cell.

* * * * *